(12) United States Patent
Gellman

(10) Patent No.: US 7,708,715 B2
(45) Date of Patent: May 4, 2010

(54) TISSUE APPROXIMATION DEVICE

(75) Inventor: Barry N. Gellman, N. Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1101 days.

(21) Appl. No.: 11/086,065

(22) Filed: Mar. 21, 2005

(65) Prior Publication Data

US 2006/0212022 A1     Sep. 21, 2006

(51) Int. Cl.
    *A61M 29/00* (2006.01)
(52) U.S. Cl. .............................. 604/96.01; 604/101.01
(58) Field of Classification Search ...... 604/96–103.14, 604/349, 544, 919, 329, 385.12, 908, 352, 604/912; 119/14.19, 14.21; 108/147.19; 135/141; 137/219; 175/321; 193/35; 206/270; 220/8; 224/521, 551; 228/154; 248/326; 267/64.26; 297/440.24; 337/247; 43/18.1; 470/4; 464/172; 5/157, 429; 52/118; 72/359; 343/883, 901; 38/102.8; 401/170; 405/294; 406/158, 167; 424/453; 606/8, 139, 153, 606/192
    See application file for complete search history.

(56) References Cited

U.S. PATENT DOCUMENTS

| | | | | |
|---|---|---|---|---|
| 2,799,273 | A | * | 7/1957 | Oddo .................... 604/101.05 |
| 4,652,258 | A | * | 3/1987 | Drach ........................ 604/540 |
| 4,873,977 | A | | 10/1989 | Avant et al. |
| 4,906,232 | A | | 3/1990 | Reynolds |
| 4,911,163 | A | * | 3/1990 | Fina ............................ 606/127 |
| 4,946,440 | A | | 8/1990 | Hall |
| 5,002,558 | A | * | 3/1991 | Klein et al. ................. 606/192 |
| 5,499,625 | A | * | 3/1996 | Frass et al. ............. 128/207.15 |
| 5,540,701 | A | | 7/1996 | Sharkey et al. |
| 5,545,171 | A | | 8/1996 | Sharkey et al. |
| 5,658,309 | A | * | 8/1997 | Berthiaume et al. ......... 606/192 |
| 5,697,943 | A | | 12/1997 | Sauer et al. |
| 5,713,889 | A | | 2/1998 | Chang |
| 5,718,686 | A | | 2/1998 | Davis |
| 5,782,800 | A | * | 7/1998 | Yoon .......................... 604/514 |
| 6,080,167 | A | | 6/2000 | Lyell |
| 6,119,697 | A | * | 9/2000 | Engel et al. ................. 128/885 |
| 6,171,281 | B1 | * | 1/2001 | Zhang ................... 604/164.01 |
| 6,254,570 | B1 | | 7/2001 | Rutner et al. |
| 6,299,598 | B1 | * | 10/2001 | Bander .................. 604/101.03 |
| 6,328,727 | B1 | | 12/2001 | Fraizer et al. |
| 6,485,456 | B1 | * | 11/2002 | Kletschka ................ 604/96.01 |

(Continued)

OTHER PUBLICATIONS

Boston Scientific Corporation, "Coude Tip Urethral Balloon Dilatation Catheter," www.bostonscientific.com, Aug. 23, 2004. (one page).

(Continued)

*Primary Examiner*—Nicholas D Lucchesi
*Assistant Examiner*—Gerald Landry, II
(74) *Attorney, Agent, or Firm*—Fay Kaplun & Marcin, LLP

(57) ABSTRACT

The invention relates to a device and method for approximating two vessels. The device includes a first catheter and a second catheter. The second catheter is slidably disposed in the first catheter. A first expansible member is disposed on the first catheter, and a second expansible member is disposed on the second catheter. The medical device also includes a locking mechanism for interlocking the first catheter and second catheter to prevent relative movement between the first and second catheters.

5 Claims, 6 Drawing Sheets

U.S. PATENT DOCUMENTS

| | | |
|---|---|---|
| 6,547,761 B2 | 4/2003 | Liu |
| 6,602,263 B1 | 8/2003 | Swanson et al. |
| 6,689,152 B2 * | 2/2004 | Balceta et al. .............. 606/200 |
| 6,692,484 B1 * | 2/2004 | Karpiel et al. .............. 604/544 |
| 6,702,825 B2 | 3/2004 | Fraizer et al. |
| 6,726,694 B2 | 4/2004 | Blatter et al. |
| 6,986,778 B2 * | 1/2006 | Zadno-Azizi .............. 606/200 |
| 7,410,481 B1 * | 8/2008 | Mitts et al. .................. 604/544 |
| 7,416,554 B2 * | 8/2008 | Lam et al. ................... 606/153 |
| 2003/0229332 A1 | 12/2003 | Intoccia |
| 2004/0044307 A1 | 3/2004 | Richardson et al. |
| 2004/0230218 A1 * | 11/2004 | Criscuolo et al. ........... 606/190 |
| 2004/0260333 A1 * | 12/2004 | Dubrul et al. ............... 606/200 |
| 2005/0131431 A1 * | 6/2005 | Copa et al. .................. 606/150 |
| 2005/0171564 A1 * | 8/2005 | Manzo ....................... 606/153 |

OTHER PUBLICATIONS

Boston Scientific Corporation, "Capio RP Suturing Device," www.bostonscientific.com, Aug. 23 2004. (9 pages).

Boston Scientific Corporation, "Coude Bardex Lubricath Latex Foley Catheters," www.bostonscientific.com, Aug. 23, 2004. (one page).

Boston Scientific Corporation, "Coude Bardex Lubricath Latex Foley Catheters," *Tour* the Bardex I.C. Catheter, Aug. 23, 2004. (two page).

Six-page International Preliminary Report on Patentability for corresponding PCT/US2006/010139.

Four-page Written Opinion for corresponding PCT/US2006/010139.

* cited by examiner

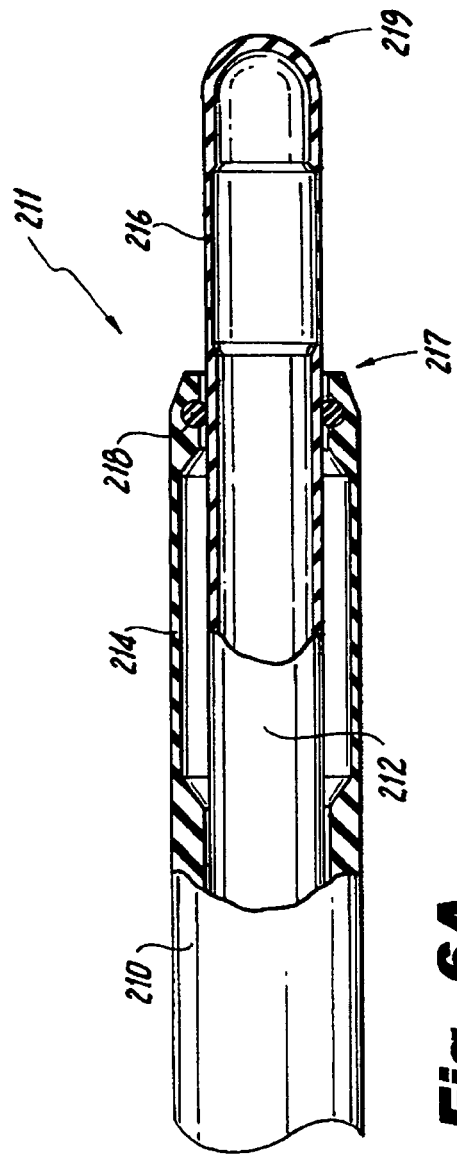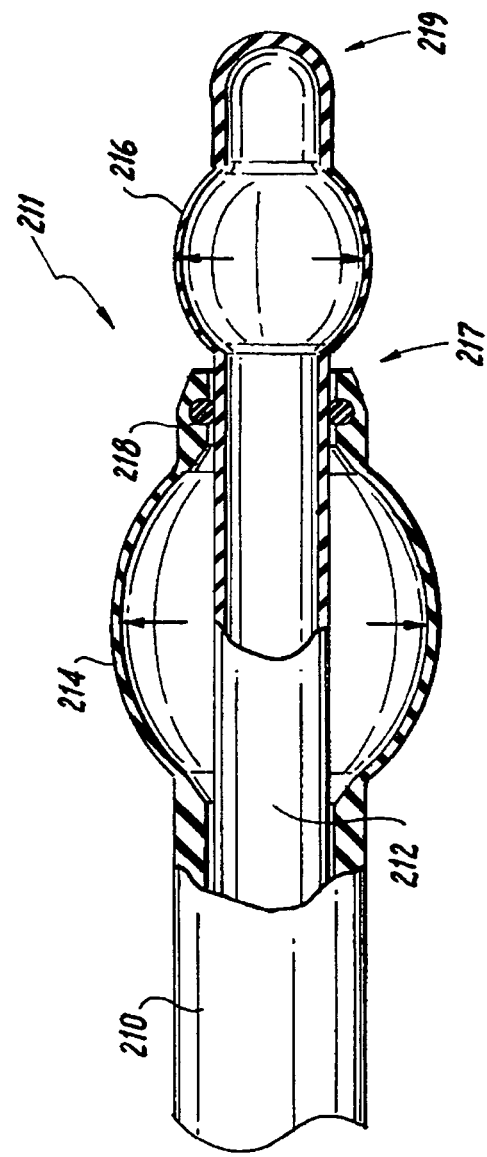
Fig. 6A
Fig. 6B

TISSUE APPROXIMATION DEVICE

TECHNICAL FIELD

The invention generally relates to a device for approximating two vessels, for example, a bladderneck to a urethral stump at the urogenital diaphragm after removal of the prostate.

BACKGROUND

Many surgical procedures require connecting vessels, hollow organs, and other structures, collectively body lumens. While some of these vessels are large and more easily manipulated by a surgeon, other body lumens are small and more difficult to manipulate and hold into position. These procedures typically use devices that employ staples, clamps, or sutures. Radical prostatectomy is an example of such a procedure.

Radical prostatectomy is an established method for treatment of patients with localized carcinoma of the prostate. Unfortunately, impotence and incontinence are frequent occurrences from many known radical prostatectomy procedures. Prostatectomy usually involves division of the urethra at the apex of the prostate and the bladder neck and removal of the prostate. After removal of the prostate, the stump of the urethra can retract into the adjacent tissue, the urogenital diaphragm, making the urethra difficult to grasp. The stump of the urethra and the bladderneck are then brought together and sutured. Most procedures performed to approximate the urethra and the bladderneck require the surgeon to grasp the end of the transected urethra and stretch it to the mating end of the bladderneck with one hand. Such grasping can cause additional trauma to the cut ends of the urethral stump and the bladderneck. Additionally, if the urogenital diaphragm is nicked during the procedure, the patient may become incontinent.

A need presently exists for apparatus and methods that facilitate approximating the urethral stump and the bladderneck after a radical prostatectomy has been performed, without traumatizing the vessels.

SUMMARY OF THE INVENTION

The invention generally relates to a device for approximating the bladderneck and the urethral stump after a radical prostatectomy. The devices and methods provide safer and less traumatic alternatives to those currently performed.

In one aspect, the invention relates to a medical device including a first catheter and a second catheter. The second catheter is slidably disposed within the first catheter. A first expansible member is disposed on the first catheter, and a second expansible member is disposed on the second catheter. The medical device also includes a locking mechanism for interlocking the first catheter and the second catheter to prevent relative movement between the first catheter and the second catheter.

In further embodiments, the second catheter includes at least one opening. In various embodiments, the second catheter includes a lumen longitudinally disposed therethrough to permit urine drainage. As an additional feature, the medical device may include a urine-drainage bag. In another embodiment, at least one of the expansible members is a balloon. As an additional feature, at least one of the expansible members is connected to at least one inflation tube.

In further embodiments, the locking mechanism includes an interlock hub with a gasket. Alternatively, the locking mechanism can be a springloaded friction lock, a one way ratchet with a release override, or a screw lock. In still another embodiment, the invention includes a handle that is coupled to the second catheter and controls the movement of the second catheter. In various embodiments, the handle is a manifold.

In another aspect, the invention features a method for approximating two vessels, such as a urethral stump and a bladderneck after being cut during a radical prostatectomy. The method includes inserting a catheter assembly that includes a first catheter and a second catheter, the second catheter slidably disposed within the first catheter. The catheter assembly further includes a first expansible member disposed about the first catheter and a second expansible member disposed about the second catheter. The first expansible member is positioned within the first vessel and expanded. The second expansible member is positioned within the second vessel by sliding the second catheter relative to the first catheter. When positioned within the second vessel, the second expansible member is expanded. With both expansible members expanded within the respective vessels, the second catheter is slid relative to the first catheter to approximate the two vessels.

In various embodiments, the method can include interlocking the first and the second catheter to maintain the relative position of the catheters. The method can also include the step of suturing the ends of the two vessels together.

In another aspect the invention relates to a medical device, including a first catheter and a second catheter. The second catheter is slidably disposed within the first catheter. A first expansible member is disposed about the first catheter, wherein the first expansible member, when expanded and in contact with an inner wall of a first vessel, provides an intraoperative seal between the first catheter and the first vessel. A second expansible member is disposed about the second catheter, wherein the second expansible member, when expanded and in contact with an inner wall of a second vessel, provides an intraoperative seal between the second catheter and the second vessel. The medical device also includes a locking mechanism for interlocking the first catheter and the second catheter to prevent relative movement between the first catheter and the second catheter.

In another aspect, the invention relates to a medical device including a first catheter and a second catheter. The first catheter includes a wall section of reduced thickness that can be expanded when exposed to increased pressure. The second catheter is slidably disposed within the first catheter. The second catheter includes a wall section of reduced thickness that can be expanded when exposed to increased pressure.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings in which:

FIGS. 6A-6B are cross-sectional views of an alternative embodiment of a medical device in accordance with the invention.

DESCRIPTION

Embodiments of the present invention are described below. The invention is not limited, however, to these embodiments. For example, various embodiments of the invention are described in terms of a urethral stump and a bladderneck; however, embodiments of the invention may be used in one or more other lumens within a body.

Figure 1:
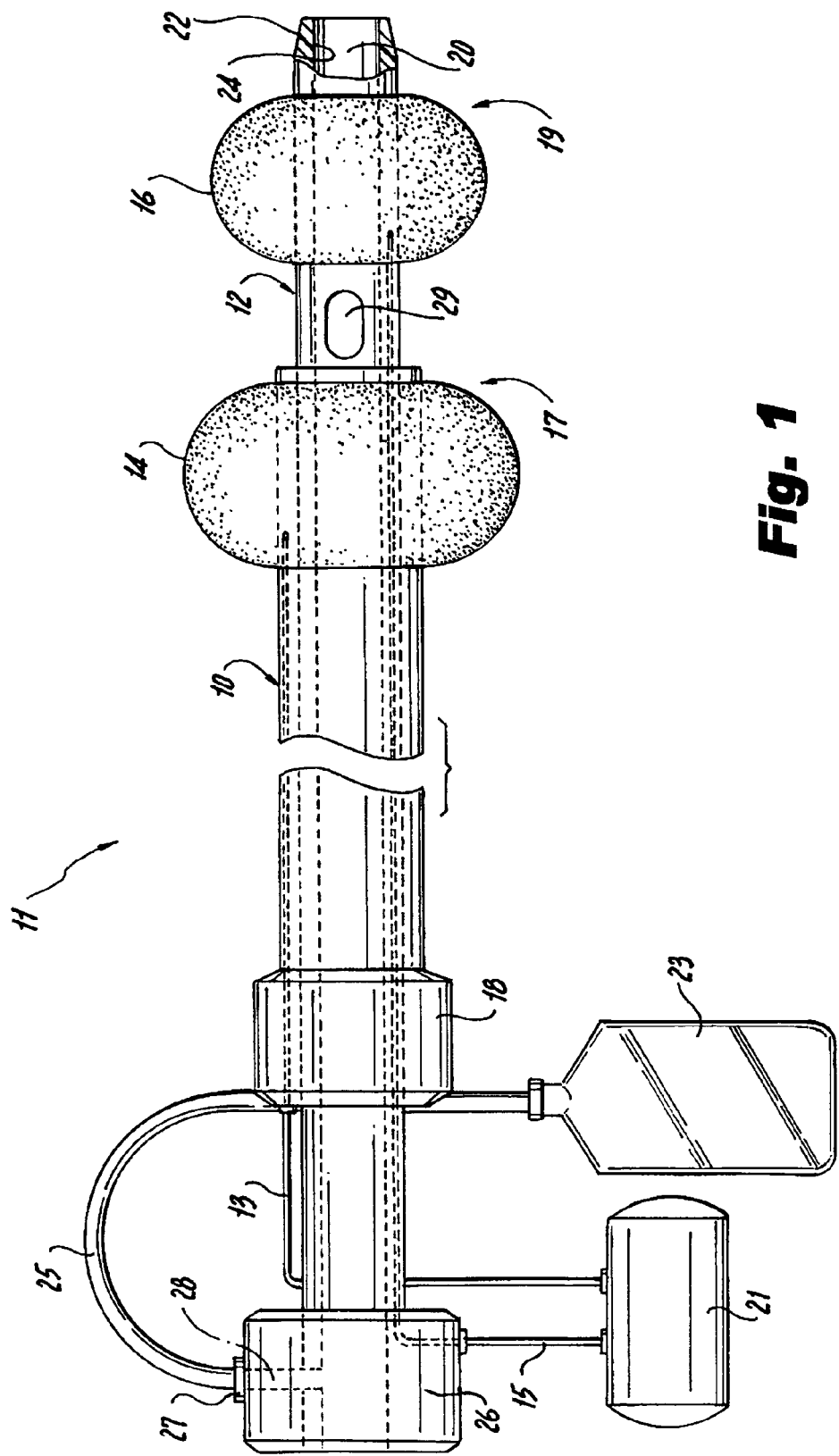
FIG. 1 is a schematic plan view of one embodiment of a medical device in accordance with the invention.

FIG. 1 illustrates one embodiment of a medical device 11 in accordance with the invention that includes a first catheter 10 and a second catheter 12. The second catheter 12 is slidably disposed within the first catheter 10. The second catheter 12 has an external surface 22 and an internal surface 24 and defines a lumen 20. The first catheter 10 defines a lumen therethrough having an inside diameter sized such that there is a close sliding fit between the first catheter 10 and the second catheter 12, allowing the catheters 10, 12 to move independently of each other. The fit between the catheters 10, 12 is such that the second catheter slides within the first catheter 10 without any play. Such a fit may provide a minimum amount of sealing between the first catheter 10 and the second catheter 12. Alternatively, or additionally, the medical device 11 could include o-rings or other means to provide a seal between the first catheter 10 and the second catheter 12 (see FIGS. 6A and 6B). Alternatively, the fit between the first catheter 10 and the second catheters 12 could be such that fluids can easily pass through the clearance between the exterior surface 22 of the second catheter 12 and the inside diameter of the first catheter 10. Furthermore, the catheters 10, 12 can include coatings on their interior and/or external surfaces to promote movement between the catheters 10, 12, such as a lubricant. In addition, coatings could be used for delivering therapeutic agents to the operative site.

The medical device 11 also includes two expansible members; a first or proximal expansible member 14 is disposed on a distal portion 17 of the first catheter 10, and a second or distal expansible member 16 is disposed on a distal portion 19 of the second catheter 12. The terms proximal and distal require a point of reference. In this application, the point of reference is the perspective of the user. Therefore, the term proximal will always refer to an area closest to the user, whereas distal will always refer to an area away from the user. In one embodiment, the expansible members 14, 16 are balloons, for example Foley type balloons. In such an embodiment, the balloons can be inflated via one or more inflation tubes.

As shown in FIG. 1, the medical device 11 includes a first tube 13 in fluid communication with the first expansible member 14 and a second tube 15 in fluid communication with the second expansible member 16. Alternatively, a single tube can be used to inflate both expansible members 14, 16. The single inflation tube may include valves to accommodate inflating the expansible members 14, 16 sequentially, as opposed to simultaneously. In addition, the tube could be slidably disposed on or within the medical device 11 to be interchangeably connected to either the first expansible member 14 or the second expansible member 16. In another embodiment, the expansible members 14, 16 can be inflated via one or more inflation channels that are formed within the first and second catheters.

The balloons 14, 16 can be inflated with a gas or a liquid, such as a saline solution or a gel. In one embodiment, the inflation tubes 13, 15 are connected to a pump 21 (i.e., syringe or pump). In one embodiment, the pump 21 can be powered by a motor. In such an embodiment, the pump 21 is a non-positive displacement pump having a preset limit. In another embodiment, the pump 21 may be a bulb type pump that is manipulated by an operator to inflate the balloons 14, 16.

The materials that can be used for the balloons 14, 16 include polymers, such as silicone, polyester, polyurethane, polyethylene terephthalate (PET), and latex. The size, shape, and length of the balloons 14, 16 will vary to suit a particular application. In one embodiment, the first balloon 14, when in the inflated position, has a diameter from about ¼ inch to about ¾ inch and a length of about 1 inch to about 1 ½ inches. The second balloon 16, when in the inflated position, has a diameter from about 1 inch to about 1 ½ inches and a length of about 1 inch to about 1 ½ inches. The shape of the balloons 14, 16 is typically spherical or annular. Alternatively, the expansible members could be a mechanical device, such as a malecot, or some other structure that is capable of engaging an interior surface of a vessel. Also, each of the expansible members could be of a different type than the other expansible member. For example, one could be a balloon and the other could be a malecot.

A locking mechanism 18 is disposed about the first catheter 10 and the second catheter 12 at a proximal end of the first catheter 10 to prevent relative movement between the first catheter 10 and the second catheter 12. In one embodiment, the locking mechanism 18 is an interlock hub with a gasket. Alternative types of locking mechanisms are a springloaded friction lock, a one way ratchet with release override, and a screw lock. One type of mechanism 18 is described in greater detail with respect to FIGS. 5A-5C.

The medical device 11 further includes a handle 26 disposed on a proximal end of the second catheter 12. The handle 26 allows the user to slide the second catheter 12 relative to the first catheter 10. As shown in FIG. 1, the handle 26 is a manifold that includes a lumen 28 disposed therethrough that is in fluid communication with the lumen 20 of the second catheter 12. In conjunction, the lumen 20 of the second catheter 12 and the lumen 28 of the handle 26 can be used for urine drainage. In such an embodiment, a drainage tube 25 can be in fluid communication with the lumen 28 of the handle 26. In one embodiment, the drainage tube 25 can be connected to the lumen 28 with a fitting 27. A urine drainage bag 23 can be coupled to the drainage tube 25.

Figure 2:
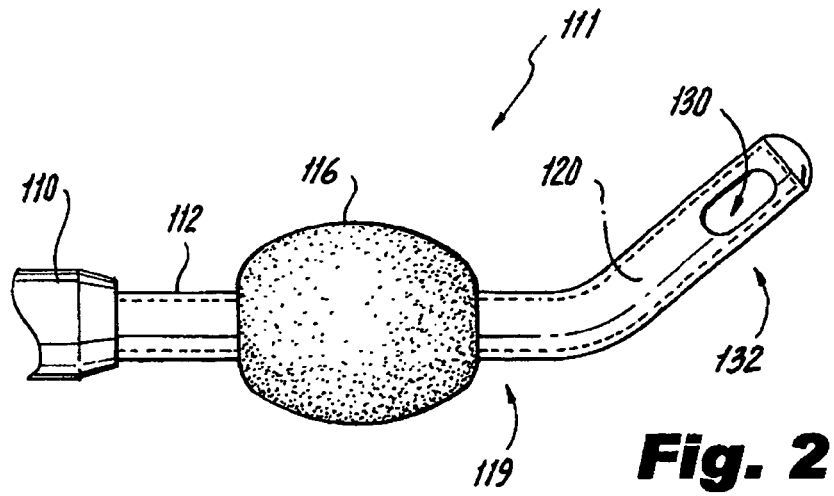
FIG. 2 is schematic side view of an alternative embodiment of a distal portion of the medical device of FIG. 1.

FIG. 2 illustrates an alternative distal portion 119 of a second catheter 112, where the distal portion 119 includes a coude tip 132 (a closed and curved tip, e.g., with a bend of about 40 degree angle). The coude tip design is smooth and facilitates passage through the urethra and the bladderneck. The tip 132 includes an opening 130 in communication with a lumen 120 of the second catheter 112. Further, the catheters 10, 12 could include multiple openings as needed for urine drainage. Additionally or alternatively, the distal end portion 119 could include a dilator to facilitate insertion of the device 111.

A variety of methods can be used to manufacture a medical device according to the invention. For example, extrusion or injection molding can be used. During extrusion, a molten state polymer is forced under high pressure through an opening, thus forming a medical device in the shape of the opening's cross-section. Initially, the solid polymer is melted by rotation of a screw and barrel under extreme heat, friction, and pressure. After the resulting molten polymer is forced through a pre-shaped die of desired cross-section, the extrudate is cooled either through immersion within a water bath or by exposure to air. In one example, extrusion may be used to provide a uniform polymeric tube, to which a hub is attached at one end and the other end is sealed.

Injection molding provides a similar means for manufacturing the medical device of the present invention. During this process, an injection unit melts the polymer and subsequently injects the melt into a hollow mold cavity of desired shape. A ram-fed injection-molding machine contains a hydraulically operated plunger. The plunger spreads a thin layer polymer into a heated region, then converges the polymer melt at a nozzle, and lastly, injects the melt into a mold. Alternatively, a reciprocation screw injection molding machine utilizes a hydraulically operated rotating screw to melt, mix, and pump the polymer, after which, the screw serves as a plunger to inject the melt into the mold. Insert molding allows the tip to be formed of a material either identical to or dissimilar from the catheter tube. Other manufacturing techniques include melting or otherwise adhering the catheter portions as components or post-forming an extruded tube.

Furthermore, various components can be bonded together by heat or solvent bonding, for example the handle 26 to the second catheter 12. Heat bonding functions by partially melting the plastic of a structure, allowing the melted plastic to adhere to a contacting surface or other component, and allowing the plastic to cool and harden, thus forming a bond. Heat bonding methods that include radio frequency bonding, induction heating, and conduction heating may be used. The plastic of a first component may be selected to melt at a similar temperature as a second component so that both components are melted during the heat bonding process. Alternatively, either the first or second component may be constructed from a plastic with a lower melting temperature than the other component in order that only the component with the lower melting temperature may melt during the bonding process. Alternatively, the components may be bonded by the use of a solvent, such as cyclohexanone and/or methylethylketone. The solvent acts by dissolving and swelling the component materials. As the component materials dissolve and swell, the components adhere to each other. The solvent is then removed allowing for the dissolved and swollen materials to harden and thus complete the bonding process.

The biocompatible materials that can be used for the various components of the medical device include polymers, such as polyurethanes, silicones, polyethylenes, nylons, polyesters, and polyester elastomers. The material hardness typically is from about 40 to about 100 durometer on Shore A scale. The size and shape of the device may vary as necessary for a particular medical application and the size of the patient. In one example, the overall outside diameter (OD) of the first catheter is from about 10 French to about 30 French. The overall length of the first catheter is from about 4 inches to about 24 inches. The OD of the second catheter is from about 8 French to about 24 French. The overall length of the second catheter is from about 6 inches to about 36 inches. In embodiments of the second catheter that include a lumen, the lumen diameter is from about 6 French to about 22 French. These dimensions are given for illustrative purposes only and are not meant to be limiting.

Figure 3A:
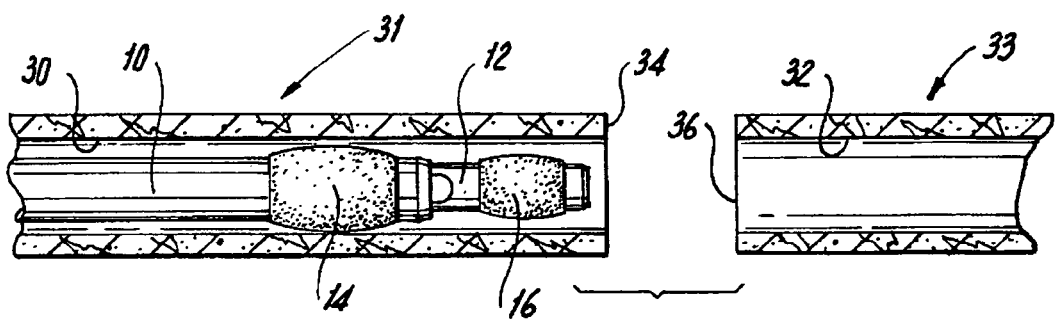
FIGS. 3A-3E are partial cross-sectional views of the medical device of FIG. 1 inserted in a body lumen; the views illustrating the steps of one embodiment of a method for approximating two vessels in accordance with the invention.
Figure 3B:
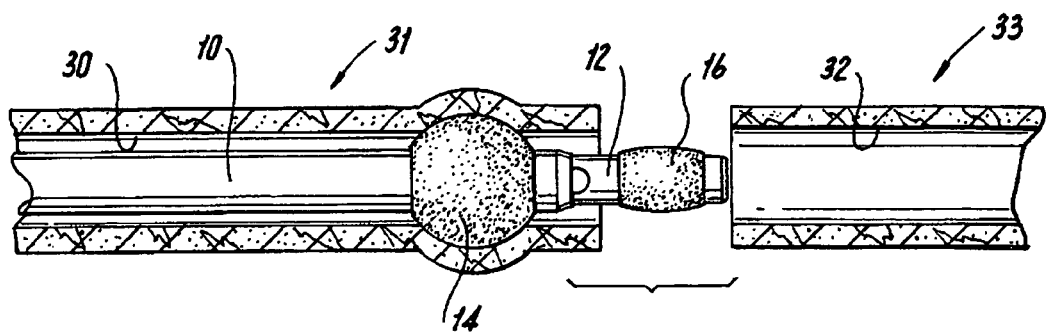
Figure 3C:
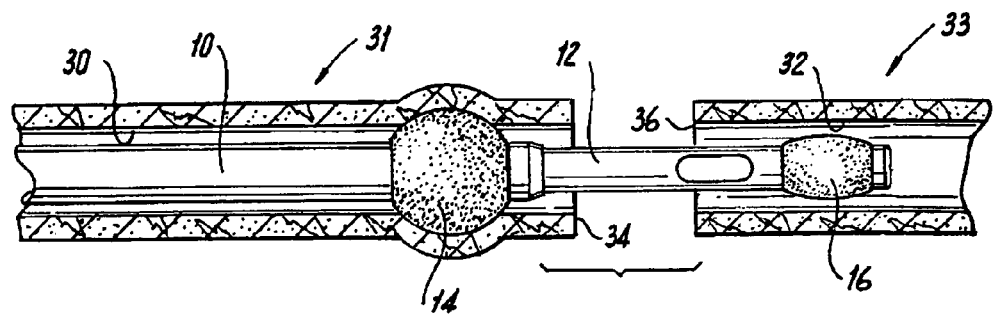
Figure 3D:
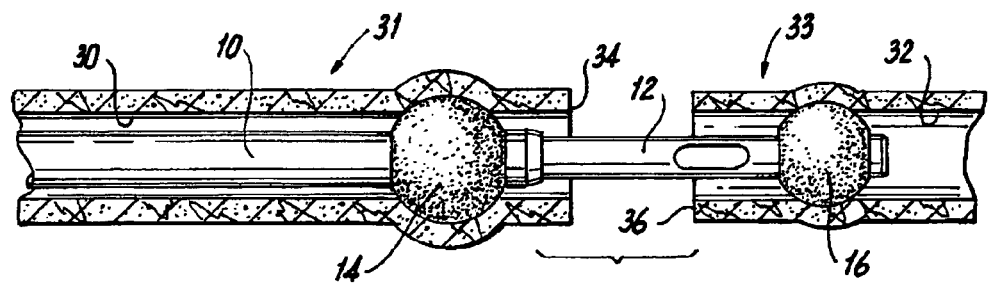
Figure 3E:
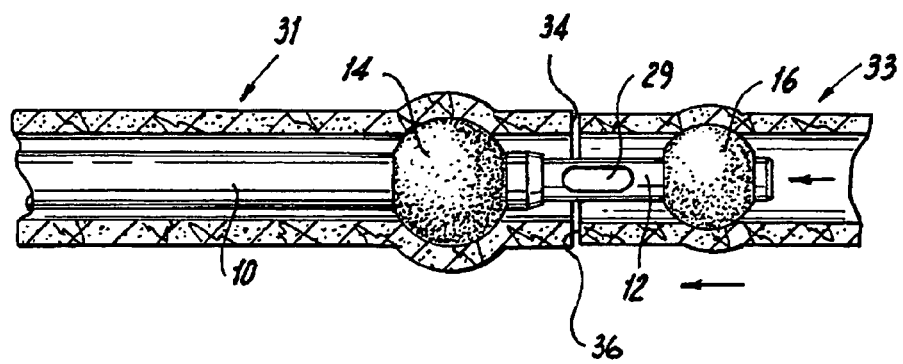
Figure 4:
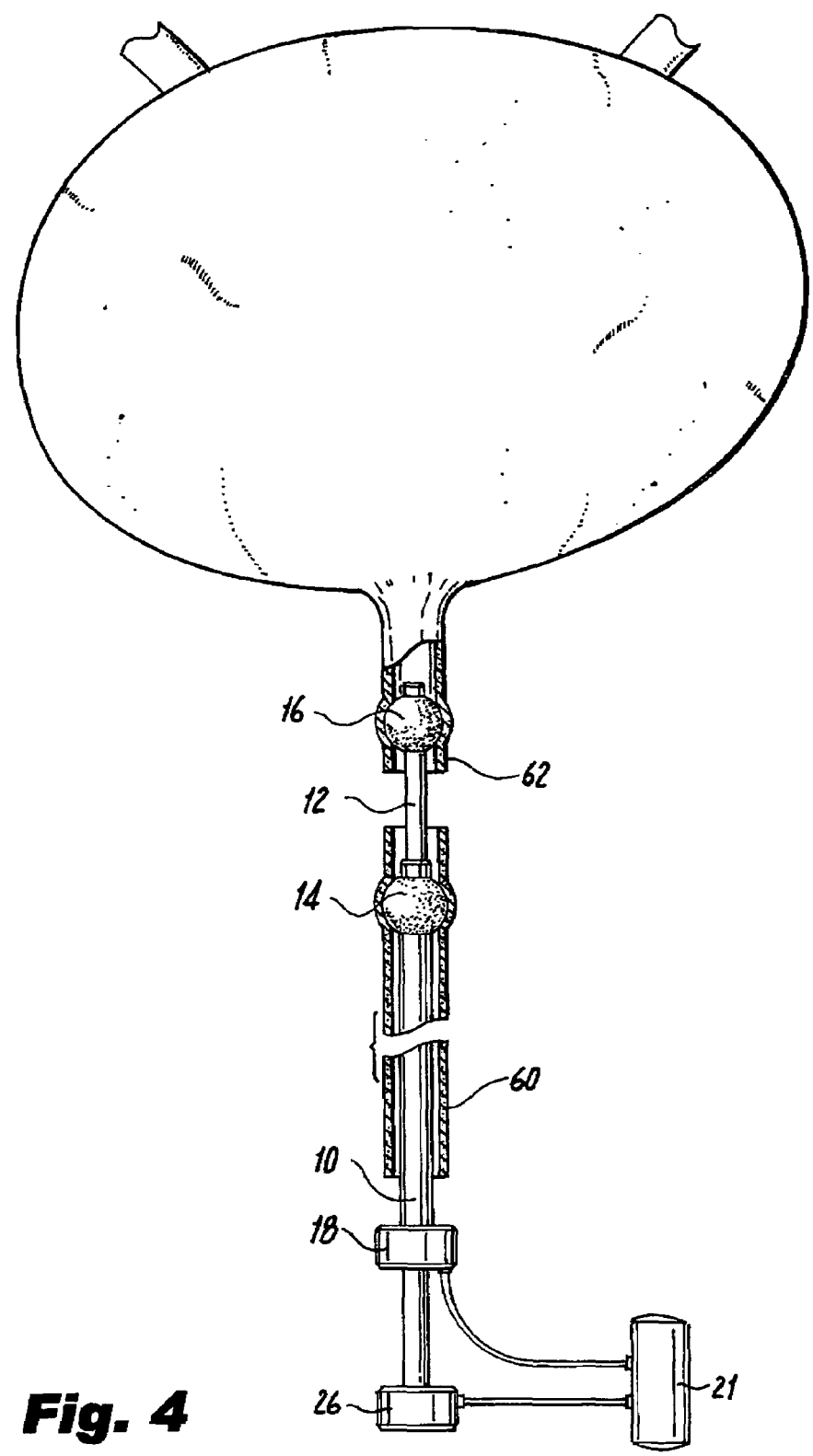
FIG. 4 is a partial cross-sectional view of one embodiment of a medical device in accordance with the invention positioned within a urethral stump and a bladderneck.

FIGS. 3A-3E depict the medical device 11 during various stages of operation. FIG. 4 illustrates the device of FIG. 1 and the method of FIGS. 3A-3E as applied to the urethral stump 60 and the bladderneck 62 after a radical prostatectomy has been performed. As shown in FIG. 3A, the medical device 111 is positioned within a lumen 30 of a first vessel 31, such as the urethral stump 60. The first expansible member 14 is expanded to secure the position of the first catheter 10 within the first lumen 30 (see FIG. 3B). Gradual inflation of the expansible member results in gradual stretching of the vessel, thereby reducing the potential for trauma, which can be caused by mechanical dilators. The expansible member, when expanded, exerts pressure against the wall of the vessel. The outward pressure and the friction between the surface of the expansible member and the wall of the vessel hold the expansible member and catheter firmly in place. The second catheter 12 is then moved distally relative to the first catheter 10 and positioned within a lumen 32 of a second vessel 33, such as a bladderneck 62 (see FIG. 3C). The second expansible member 16 is expanded to secure the position of the second catheter 12 within the second lumen 32 (see FIG. 3D). The second catheter 12 is slid relative to the first catheter 10 to approximate the two vessels 31, 33 by drawing the vessels 31, 33 together. In one embodiment, the first catheter 10 and second catheter 12 can be interlocked before expanding the second expansible member 16 to maintain the position of the second catheter 12 within the second vessel 32. After the second expansible member 16 is expanded, the catheters 10, 12 are unlocked and moved relative to each other to approximate the first and the second vessels 31, 33 (see FIG. 3E).

In one embodiment, the expansible members 14, 16 can be positioned at the ends 34, 36 of the vessels 31, 33 allowing a user to bring the ends 34, 36 of the vessels 31, 33 tightly together. In another embodiment, the expansible members 14, 16 can be positioned a small distance away from the ends 34, 36 of the vessels 31, 33 leaving a larger distance between the expansible members 14, 16. This larger distance facilitates the use of a suturing device to approximate the vessel ends 34, 36.

In one embodiment, the urethral stump 31 can be pushed distally to elongate the urethral stump 31 to aid in suture placement about the urethral periphery. In another embodiment, the second catheter 12 can be pulled proximally to draw the bladderneck 33 closer to the urethral stump 31. This embodiment reduces trauma to the cut ends of the urethra, which can be caused by reducing the grasping of the tissue. Once the two vessels 31, 33 are approximated, the first catheter 10 and second catheter 12 can be interlocked to prevent the catheters 10, 12 from moving and, thus, maintaining contact between the two vessel ends 34, 36. While held together, the two vessels 31, 33 can be sutured together or can be allowed to heal naturally without suturing. Alternatively, the sutures may be applied to the urethra and bladderneck in advance of balloon retraction and guided together slowly, snugging the sutures while the device maintains traction. The medical device 11 can be easily removed from a patient by collapsing the expansible members and then withdrawing the medical device 11 from the patient.

The spacing between the expansible members 14, 16 can be adjusted by sliding the catheters 10, 12 relative to each other. The variable spacing between the expansible members can be advantageous in situations where extra space is required to permit suturing. Suturing can be performed, for example, with a Capio RP® suturing device available from Boston Scientific Corporation. In some embodiments, the second catheter 12 may include an opening 29 through which an end of the suturing device may extend, the suturing device being placed within the lumen 20 of the second catheter 12. The opening 29 may be positioned relative to the area to be sutured by sliding and/or rotating the second catheter 12. The opening 29 should be sized to permit the end of the suturing device to extend through the opening without any restriction. Additionally or alternatively, other instruments can be used to access the area surrounding the ends of the vessels 34, 36 for viewing or performing other procedures.

The medical device 11 can be used in Laparoscopic Radical Prostatectomy (LRP). A LRP procedure is done through several small incisions in the abdomen, rather than a large, open one. Specially designed surgical instruments and cameras afford the surgeon precise control and excellent visibility for performing the operation. During laparoscopic procedures, a thin needle is placed into the abdomen through which carbon dioxide gas is introduced to inflate the abdominal cavity to give the surgeon visibility and space to work. The surgical openings created by removal of the prostate could result in gas leakage. In one embodiment, the first balloon 14, when expanded and in contact with the wall of the urethral stump, provides an intraoperative urethra to catheter seal that reduces gas loss. In a further embodiment, the second balloon 16, when expanded and in contact with the wall of the bladderneck, provides an intraoperative bladderneck to catheter seal that reduces gas loss. Additionally, when the two balloons are approximated, the second balloon 16 can be compressed against the distal end of the first catheter 10 providing a seal, thereby reducing gas leakage. In another embodiment, the first balloon 14 can be compressed around the second catheter 12 to reduce gas leakage. In another embodiment, the first catheter 10 can include at least one o-ring (or other means) disposed at the distal end 17 of the first catheter 10 to provide a seal between the first catheter 10 and the second catheter 12 to reduce gas leakage.

Figure 5A:
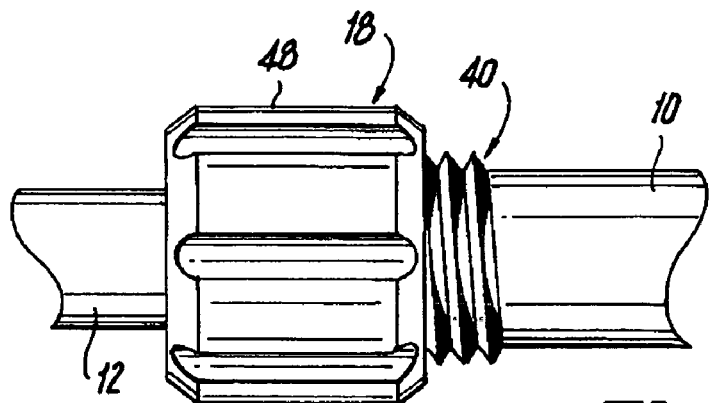
FIGS. 5A-5C are schematic plan views of one embodiment of a locking mechanism in accordance with the invention.
Figure 5B:
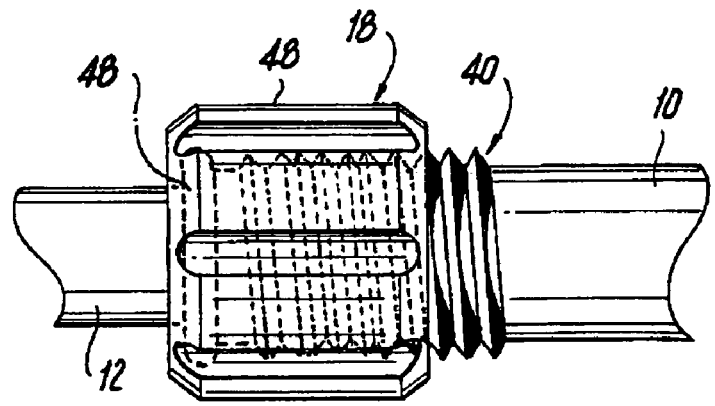
Figure 5C:
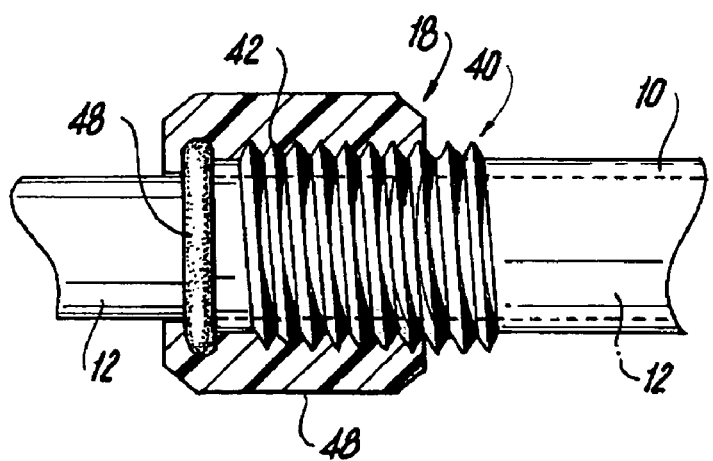

FIGS. 5A-5C illustrate the screw lock embodiment of the locking mechanism 18. The locking mechanism 18 comprises an interlock hub 48 with an internal thread 42 and a gasket 44. A portion of the proximal end of the first catheter 10 has an external thread 40. The interlock hub 48 has a lumen disposed longitudinally therethrough for receiving the first catheter 10 and through which the second catheter 12 is slidably disposed. The gasket 44 has a hole defined therein through which the second catheter 12 is slidably disposed. When the user advances the locking mechanism 18, the gasket 44 compresses against the proximal end of the first catheter 10, which simultaneously causes the gasket to expand inwardly against the surface of the second catheter 12, causing a pressure seal on the second catheter 12 and interlocking the two catheters 10, 12. The gasket 44 may be made of a number of suitable materials such as rubber or latex. Alternatively, the first catheter 10 and the second catheters 12 can be interlocked by using a set screw that is threaded through the first catheter 10 and contacts the second catheter 12 to prevent relative movement thereof. In addition, the external threaded portion 40 of the first catheter 10 could be tapered, such that when the hub 48 is tightened, the first catheter 10 is compressed against the second catheter 12.

FIGS. 6A and 6B illustrate an alternative embodiment of a medical device 211 in accordance with the invention. The medical device 211 is similar to the device 11 described with respect to FIGS. 1, 3A-3E, 4, and 5A-5C. The medical device 211 includes a first catheter 210 and a second catheter 212. The second catheter 212 is slidably disposed within the first catheter 210. The first catheter 210 defines a lumen therethrough and the diameter of the first catheter 210 is such that there is a close sliding fit between the first catheter 210 and the second catheter 212 allowing the catheters to move independently of each other. The second catheter defines a lumen therethrough. A locking mechanism as previously described could also be used with this embodiment to prevent relative movement between the first catheter 210 and the second catheter 212. The first catheter 210 includes a wall section 214 of reduced thickness that can be expanded when exposed to an increase in pressure (see FIG. 6B). The second catheter 212 includes a wall section 216 of reduced thickness that can be expanded when exposed to increased pressure (see FIG. 6B). When exposed to an increased pressure, wall sections 214, 216 bulge outward and exert pressure against the wall of a vessel. The outward pressure and the friction between the bulging wall sections 214, 216 and the wall of the vessel hold the catheter firmly in place. The distal end 219 of the second catheter 212 is closed thus preventing loss of pressure when the wall section 216 is expanded. The first catheter 210 includes at least one o-ring 218 (or other means) disposed at the distal end 217 of the first catheter 210 to provide a seal between the first catheter 210 and the second catheter 212. This seal prevents loss of pressure when the wall section 214 is expanded.

The materials and methods of manufacture that can be used for the medical device 211 are discussed hereinabove with respect to the medical device 11. In one example, a catheter having a constant wall thickness can be formed by extrusion and the reduced thickness of a wall section can be achieved by machining the catheter. The thickness of the wall sections 214, 216 varies with the type of material. The thickness of the wall sections 214, 216 will be greater for a material with increased elasticity and smaller for a material with less elasticity.

Having described certain embodiments of the invention, it will be apparent to those of ordinary skill in the art that other embodiments incorporating the concepts disclosed herein may be used without departing from the spirit and scope of the invention. The described embodiments are to be considered in all respects as only illustrative and not restrictive.

What is claimed is:

1. A method for approximating a first vessel and a second vessel comprising:
   inserting a catheter assembly comprising a first catheter, a second catheter slidably disposed within the first catheter, a first balloon disposed about the first catheter, a second balloon disposed about the second catheter, and a locking mechanism for interlocking the first catheter and the second catheter;
   positioning the first balloon within the first vessel;
   inflating the first balloon;
   positioning the second balloon within the second vessel by sliding the second catheter relative to the first catheter;
   inflating the second balloon within the second vessel;
   sliding the second catheter relative to the first catheter for approximating the two vessels; and
   engaging the locking mechanism causing a pressure seal on the second catheter and preventing relative movement between the first catheter and the second catheter.

2. The method of claim 1, wherein the first vessel is a urethral stump and the second vessel is a bladderneck.

3. The method of claim 1, wherein at least one inflation tube is connected to at least one of the first balloon and the second balloon.

4. The method of claim 1, further comprising the step of suturing the ends of the two vessels together.

5. The method of claim 1, wherein the locking mechanism comprises an interlock hub with a gasket.

* * * * *